(12) United States Patent
Dekrom

(10) Patent No.: US 8,080,594 B2
(45) Date of Patent: Dec. 20, 2011

(54) TIME-RELEASE DENTAL ADHESIVE

(75) Inventor: Adrian Dekrom, Chagrin Falls, OH (US)

(73) Assignees: Thomas R. Haddix, Monroe, MI (US); Steven J. Haddix, Allen Park, MI (US)

( * ) Notice: Subject to any disclaimer, the term of this patent is extended or adjusted under 35 U.S.C. 154(b) by 0 days.

(21) Appl. No.: 12/662,444

(22) Filed: Apr. 16, 2010

(65) Prior Publication Data

US 2011/0257293 A1 Oct. 20, 2011

(51) Int. Cl.
*A61K 6/097* (2006.01)

(52) U.S. Cl. .................. 523/116; 433/228.1; 106/35

(58) Field of Classification Search .................. 523/115, 523/116, 117; 433/228.1; 106/35
See application file for complete search history.

(56) References Cited

U.S. PATENT DOCUMENTS

| | | | | |
|---|---|---|---|---|
| 4,141,864 A | * | 2/1979 | Rijke et al. ................ | 523/114 |
| 4,189,838 A | * | 2/1980 | Oliva ........................ | 433/167 |
| 4,318,742 A | * | 3/1982 | Lokken ..................... | 106/35 |
| 4,370,401 A | * | 1/1983 | Winslow et al. ........... | 430/178 |
| 4,759,798 A | * | 7/1988 | von Nostitz ............... | 106/35 |
| 5,202,181 A | * | 4/1993 | Hara et al. ................. | 428/350 |
| 5,225,315 A | * | 7/1993 | Grosclaude et al. ....... | 430/270.1 |
| 5,298,534 A | * | 3/1994 | Prosise et al. ............. | 523/120 |
| 5,388,754 A | * | 2/1995 | Grosclaude et al. ....... | 228/118 |
| 5,391,589 A | * | 2/1995 | Kiguchi et al. ............ | 523/106 |
| 5,580,940 A | * | 12/1996 | Oosterhoff ................. | 526/238.23 |
| 5,810,595 A | | 9/1998 | Mallow | |
| 5,994,484 A | * | 11/1999 | Pocius ....................... | 526/196 |
| 6,008,308 A | * | 12/1999 | Pocius ....................... | 526/196 |
| 6,093,778 A | * | 7/2000 | Pocius ....................... | 526/196 |
| 6,217,894 B1 | * | 4/2001 | Sawhney et al. ........... | 424/426 |
| 6,306,206 B1 | * | 10/2001 | Fischer et al. ............. | 106/35 |
| 6,353,041 B1 | * | 3/2002 | Qian ......................... | 523/116 |
| 6,355,704 B1 | | 3/2002 | Nakatsuka et al. | |
| 6,583,197 B1 | * | 6/2003 | Wada et al. ................ | 522/84 |
| 6,649,669 B2 | | 11/2003 | Dickens | |
| 6,750,268 B2 | | 6/2004 | Hino | |
| 6,814,794 B2 | * | 11/2004 | Allred ....................... | 106/35 |
| 0,299,157 A1 | | 12/2007 | Sang et al. | |
| 7,304,096 B2 | | 12/2007 | Han et al. | |
| 0,004,365 A1 | | 1/2008 | Blackwell | |
| 7,476,448 B2 | * | 1/2009 | Natsui et al. .............. | 428/532 |
| 2006/0216537 A1 | * | 9/2006 | Natsui et al. .............. | 428/537.5 |
| 2007/0183936 A1 | * | 8/2007 | Newsam et al. ........... | 422/102 |
| 2010/0321430 A1 | * | 12/2010 | Koganehira et al. ....... | 347/9 |

FOREIGN PATENT DOCUMENTS

| | | |
|---|---|---|
| EP | 1287805 | 3/2003 |
| JP | 5-286822 | 11/1993 |
| JP | 9-157126 | 6/1997 |

* cited by examiner

*Primary Examiner* — Robert J Hill, Jr.
*Assistant Examiner* — Peter A Salamon
(74) *Attorney, Agent, or Firm* — Richard C. Litman

(57) ABSTRACT

The time-release dental adhesive is made as a two-part preparation to increase shelf life. The first part contains three monomers (hydroxyethyl methacrylate [HEMA], triethyleneglycol dimethacrylate [TEG-DMA], and bisphenol A di(ethyl-methacrylate) [BPA-DEMA]), glycerol, a polymerization catalyst, a filler, and a stabilizer. The second part contains the same three monomers listed above, an acrylic resin to increase viscosity, an accelerator, a filler, and a sugar or sugar-based sweetener. When desired for use, the two parts are mixed in a 1:1 ratio by weight. The adhesive cures to a strong, hard bonding agent, but gradually weakens in the presence of moisture to provide a time-release adhesive. The amount of elapsed time before release of the adhesive may be controlled by changing the quantity of sugar or sugar-based sweetener in the adhesive.

16 Claims, No Drawings

TIME-RELEASE DENTAL ADHESIVE

BACKGROUND OF THE INVENTION

1. Field of the Invention

The present invention relates to adhesives, and particularly to a time-release dental adhesive for bonding to teeth for a limited period of time, or for bonding two materials together for a limited period of time.

2. Description of the Related Art

Dental adhesives for restorations and repair are well known. However, such adhesives are used with a cement and are formulated for permanent adhesion. Denture adhesives are designed for temporary use. However, denture adhesives are generally formulated for adhesion between the plate and the roof of the mouth, and while strong enough to hold dentures in the mouth, are not strong enough for other applications, e.g., for holding upper and lower teeth together.

There are some applications where it is desired to adhere a material to the teeth for a limited period of time. For example, U.S. Pat. No. 7,185,654, issued Mar. 6, 2007 to Haddix et al., describes a system for preventing snoring that employs a tape that adheres to the teeth to secure the lower and upper teeth together to keep the mouth closed during sleep to prevent snoring. Similarly, it may be desired to adhere the teeth together for a limited period of time to prevent snacking between meals, to adhere a decoration or appliance to the teeth for a limited period of time, etc.

Thus, a time-release dental adhesive solving the aforementioned problems is desired.

SUMMARY OF THE INVENTION

The time-release dental adhesive is made as a two-part preparation to increase shelf life. The first part contains three monomers (hydroxyethyl methacrylate [HEMA], triethyleneglycol dimethacrylate [TEG-DMA], and bisphenol A di(ethyl-methacrylate) [BPA-DEMA]), an acrylic resin, glycerol, a polymerization initiator or catalyst, a filler, and a stabilizer. The second part contains the same three monomers listed above, an acrylic resin to increase viscosity, a curing agent or accelerator, a filler, and a sugar or sugar-based sweetener. When desired for use, the two parts are mixed in a 1:1 ratio by weight. The adhesive cures to a strong, hard bonding agent, but gradually weakens in the presence of moisture to provide a time-release adhesive. The amount of elapsed time before release of the adhesive may be controlled by changing the quantity of sugar or sugar-based sweetener in the adhesive.

The time-release dental adhesive is suitable for application to a tape used to secure upper and lower teeth together while sleeping to prevent snoring, to bond the teeth together to prevent snacking between meals, and for other applications where it is desired to bond two materials together for a controlled period of time in an environment where the adhesive is exposed to moisture.

These and other features of the present invention will become readily apparent upon further review of the following specification.

DETAILED DESCRIPTION OF THE PREFERRED EMBODIMENTS

The time-release dental adhesive is made as a two-part preparation to increase shelf life. The first part contains three monomers (hydroxyethyl methacrylate [HEMA], triethyleneglycol dimethacrylate [TEG-DMA], and bisphenol A di(ethyl-methacrylate) [BPA-DEMA]), an acrylic resin, glycerol, a polymerization initiator or catalyst, a filler, and a stabilizer. The second part contains the same three monomers listed above, an acrylic resin to increase viscosity, a curing agent or accelerator, a filler, and a sugar or sugar-based sweetener. When desired for use, the two parts are mixed in a 1:1 ratio by weight. The adhesive cures to a strong, hard bonding agent, but gradually weakens in the presence of moisture to provide a time-release adhesive. The amount of elapsed time before release of the adhesive may be controlled by changing the quantity of sugar or sugar-based sweetener in the adhesive.

The time-release dental adhesive is suitable for application to a tape used to secure upper and lower teeth together while sleeping to prevent snoring, to bond the teeth together to prevent snacking between meals, and for other applications where it is desired to bond two materials together for a controlled period of time in an environment where the adhesive is exposed to moisture.

The time-release dental adhesive will be better understood by the following example showing preparation of the adhesive.

EXAMPLE

A sample of the time-release dental adhesive was prepared as follows. First, a resin concentrate was prepared. The resin concentrate contained about 60% by weight acrylic monomer, namely, hydroxyethyl methacrylate (HEMA) and about 40% by weight acrylic resin, e.g., Paraloid™ B-66, made by Rohm and Haas. Paraloid B-66 was slowly added to the HEMA under shear and mixed until soluble.

Next, an initiator concentrate was prepared. The initiator concentrate included a peroxide initiator or catalyst, e.g., benzoyl peroxide, and a low boiling point solvent, viz., diethyl ether. The initiator concentrate contained about 4% initiator to 96% solvent, by weight. The initiator was added to the solvent with slow mixing.

The first part was prepared as follows. Ethyl methacrylate was placed in a container and the acrylic resin, Paraloid B-66, was dissolved in the acrylic monomer. A first acrylic oligomer, triethyleneglycol dimethacrylate (Sartomer SR-205); a second acrylic oligomer, bisphenol A di(ethyl-methacrylate), (viz., Sartomer 348), glycerine, and the stabilizer (Tinuvin 328, made by Ciba, chemical name 2-(2H-benzotriazol-2-yl)-4,6-ditertpentylphenol) were added to the mixture of the acrylic monomer and acrylic resin. A fumed silica filler (Syloid 244) was slowly added to this mixture under high shear. The batch was cooled to room temperature and the initiator concentrate (benzoyl peroxide in diethyl ether) was added. Finally, the diethyl ether solvent was stripped from the mixture. The first part had the composition shown in Table I.

TABLE I

Components in the First Part

| Chemical Name | Weight % |
|---|---|
| Ethyl Methacrylate/Acrylic resin | 81 |
| Triethyleneglycol dimethacrylate | 3.3 |
| Bisphenol A di(ethyl-methacrylate) | 1.7 |
| Glycerol | 4.3 |
| 2-(2H-benzotriazol-2-yl)-4,6-ditertpentylphenol (Tinuvin 328) | 0.05 |
| Fumed silica | 7.2 |
| Benzoyl peroxide | 2.5 |

The second part was prepared as follows. The resin concentrate and the two acrylic oligomers (triethyleneglycol dimethacrylate and bisphenol A di(ethyl-methacrylate)) were placed in a suitable container. The sugar or sugar-based sweetener used in this example was Splenda® (Splenda is a registered trademark of McNeil Nutritionals, LLC of Fort Washington, Pa.), which contains about 95% dextrose and maltodextrin, and a small amount of sucralose (1',4,6'-trichlorogalactosucrose or simply trichlorosucrose). However, sucrose or similar sugars should have the same effect in causing the time-release dental adhesive to weaken and release in the presence of moisture. Splenda, the accelerator (dimethyl analine) and fumed silica filler were added to the mixture of the resin concentrate and the acrylic oligomers. The composition of the second part before addition of the Splenda is shown in Table II.

TABLE II

| Components in the Second Part | |
| --- | --- |
| Chemical Name | Weight % |
| HEMA/Paraloid B-66 (resin concentrate) | 86.7 |
| Triethyleneglycol dimethacrylate | 2.1 |
| Bisphenol A di(ethyl-methacrylate) | 1.3 |
| Dimethyl analine | 2.7 |
| Fumed silica | 7.2 |

The amount of Splenda added was adjusted to change the time-release property. When Splenda was added to form 1 wt. % of the second part, the adhesive was hard to remove, having a longer release time. When Splenda was added to form 3 wt. % of the second part, the adhesive had a moderate release time. When Splenda was added to form 5 wt. % of the second part, the adhesive falls off quicker, having a quicker release time. Thus, the release time can be adjusted by adjusting the quantity of sugar or sugar-based sweetener in the composition. For example, the composition of the time-release dental adhesive can be adjusted to release after 8 hours to prevent snoring when applied to the tape described in U.S. Pat. No. 7,185,654, or to 4 hours when used as a deterrent to snacking between meals, simply by adjusting the quantity of sugar or sugar-based sweetener in the adhesive.

To use the adhesive, the first part is mixed with the second part in a 1:1 ratio.

Although described with respect to oral or dental use, the time-release adhesive may also be used for any application, whether personal, commercial, or industrial where it is desired to bond two materials together for a controlled period of time in an environment where the adhesive is exposed to moisture.

It is to be understood that the present invention is not limited to the embodiments described above, but encompasses any and all embodiments within the scope of the following claims.

I claim:

1. A time-release adhesive, comprising a two-part formulation forming a polymer adhesive when the two parts are mixed in a 1:1 ratio by weight, wherein the two-part formulation comprises:
   i) a first part having a first plurality of polymerizable acrylic monomers, glycerol, an acrylic resin, and a polymerization catalyst; and
   ii) a second part having a second plurality of polymerizable acrylic monomers, an acrylic resin, and a polymerization accelerator, wherein the polymerization accelerator comprises dimethyl analine;
   the formulation further including a quantity of a sugar or a sugar-based sweetener,
   whereby the adhesive curing to form a hard bond between the two materials, the bond weakening and releasing in the presence of moisture after a period of time controlled by the quantity of the sugar or sugar-based sweetener.

2. The time-release adhesive according to claim 1, wherein said sugar or sugar-based sweetener comprises sucralose.

3. The time-release adhesive according to claim 1, wherein said first and second plurality of polymerizable acrylic monomers comprise hydroxyethyl methacrylate, triethyleneglycol dimethacrylate, and bisphenol A di(ethyl-methacrylate).

4. The time-release adhesive according to claim 1, wherein said polymerization catalyst comprises benzoyl peroxide.

5. The time-release adhesive according to claim 1, wherein said first part further comprises stabilizer for an acrylic polymer.

6. The time-release adhesive according to claim 5, wherein said stabilizer comprises 2-(2H-benzotriazol-2-yl)-4, 6-ditertpentylphenol.

7. The time-release adhesive according to claim 1, wherein said first part further comprises a filler.

8. The time-release adhesive according to claim 7, wherein said filler comprises fumed silica.

9. The time-release adhesive according to claim 1, wherein said second part further comprises a filler.

10. The time-release adhesive according to claim 9, wherein said filler comprises fused silica.

11. The time-release adhesive according to claim 1, wherein said sugar or sugar-based sweetener comprises an artificial sweetener including:
   about 95% by weight dextrose and maltodextrin; and
   sucralose.

12. A time-release adhesive, comprising a formulation having a first part and a second part, wherein:
   the first part has a first plurality of polymerizable acrylic monomers, glycerol, an acrylic resin, and a polymerization catalyst; and
   a second part having a second plurality of polymerizable acrylic monomers, an acrylic resin, a polymerization accelerator, and a sugar-based artificial sweetener, wherein the sugar-based artificial sweetener comprises sucralose, the first and second parts polymerizing to form a hard adhesive bond when mixed, the hard adhesive bond releasing in the presence of moisture after a period of time determined by the quantity of the sugar-based artificial sweetener.

13. The time-release adhesive according to claim 12, wherein said sugar-based artificial sweetener comprises about 95% by weight dextrose and maltodextrin, and sucralose.

14. The time-release adhesive according to claim 12, wherein said first part further comprises fumed silica filler and a stabilizer.

15. The time-release adhesive according to claim 12, wherein said catalyst comprises benzoyl peroxide and said accelerator comprises dimethyl analine.

16. A time-release adhesive, comprising a formulation having a first part and a second part, wherein:
   the first part includes:
   hydroxyethyl methacrylate;
   triethyleneglycol dimethacrylate;
   bisphenol A di(ethyl-methacrylate);
   glycerol;
   an acrylic resin;
   a filler;
   a stabilizer; and benzoyl peroxide; and
the second part includes:
hydroxyethyl methacrylate;
triethyleneglycol dimethacrylate;
bisphenol A di(ethyl-methacrylate);
an acrylic resin;
dimethyl analine;
a filler; and
sucralose, the first and second parts polymerizing to form a hard adhesive bond when mixed in a 1:1 ratio by weight, the hard adhesive bond releasing in the presence of moisture after a period of time determined by the quantity of the sucralose.

* * * * *